(12) United States Patent
Marti

(10) Patent No.: US 10,071,208 B2
(45) Date of Patent: Sep. 11, 2018

(54) DEVICE FOR REDUCING THE PAIN ASSOCIATED WITH INSERTION OF SYRINGE NEEDLE INTO THE SKIN

(71) Applicant: Karim-Frederic Marti, Le Landeron (CH)

(72) Inventor: Karim-Frederic Marti, Le Landeron (CH)

(*) Notice: Subject to any disclaimer, the term of this patent is extended or adjusted under 35 U.S.C. 154(b) by 0 days.

(21) Appl. No.: 14/022,992

(22) Filed: Sep. 10, 2013

(65) Prior Publication Data
US 2014/0074025 A1 Mar. 13, 2014

(30) Foreign Application Priority Data
Sep. 11, 2012 (EP) .................................... 12183927

(51) Int. Cl.
| A61M 5/00 | (2006.01) |
| A61M 5/42 | (2006.01) |
| A61M 5/32 | (2006.01) |
| A61M 5/31 | (2006.01) |

(52) U.S. Cl.
CPC .......... *A61M 5/422* (2013.01); *A61M 5/3243* (2013.01); *A61M 5/3287* (2013.01); *A61M 5/3137* (2013.01)

(58) Field of Classification Search
CPC ........ A61M 5/422; A61M 5/433; A61M 5/42; A61M 5/142; A61M 5/1422; A61M 5/137; A61M 5/3293; Y10S 514/817
USPC .................................................. 604/112–117
See application file for complete search history.

(56) References Cited

U.S. PATENT DOCUMENTS

| 5,013,545 A | * | 5/1991 | Blackman et al. ........... 514/716 |
| 5,496,288 A | * | 3/1996 | Sweeney ............... A61M 5/178 |
| | | | 220/254.3 |
| 5,989,567 A | * | 11/1999 | Dolisi .......................... 424/400 |
| 6,200,291 B1 | * | 3/2001 | Di Pietro ..................... 604/117 |

(Continued)

FOREIGN PATENT DOCUMENTS

| CH | 693 259 A5 | 5/2003 |
| DE | 10 2010 046 560 A1 | 3/2012 |

(Continued)

OTHER PUBLICATIONS

European Search Report dated Mar. 27, 2013, in Patent Application No. EP 12 18 3927, filed Sep. 11, 2012 (With English-language Translation).

*Primary Examiner* — Kevin C Sirmons
*Assistant Examiner* — Tiffany Legette-Thompson
(74) *Attorney, Agent, or Firm* — Oblon, McClelland, Maier & Neustadt, L.L.P.

(57) ABSTRACT

The device allows the pain associated with the insertion of a needle of a syringe into the skin to be reduced. To do this, this device comprises a sleeve, which has a first rear portion to at least partially receive the syringe with the needle and a second front portion fitted with an end part, through which an opening passes for passage of the needle. A front face of the end part is intended to be applied with pressure against the skin of a person before insertion of the needle into the skin. This front face of the end part is arranged to receive an active substance for desensitizing the skin. The active substance can be applied to the skin at the instant the terminal part presses on the penetration site to desensitize the skin.

14 Claims, 3 Drawing Sheets

(56) References Cited

U.S. PATENT DOCUMENTS

| | | | |
|---|---|---|---|
| 6,312,412 B1* | 11/2001 | Saied et al. .................... 604/191 |
| 2002/0133138 A1* | 9/2002 | Pyret ........................ A61D 7/00 604/506 |
| 2003/0054017 A1* | 3/2003 | Castillo ................ A61K 9/0014 424/400 |
| 2003/0073960 A1* | 4/2003 | Adams ............... A61B 17/3417 604/268 |
| 2006/0127429 A1* | 6/2006 | McCartt ............... A61K 9/0014 424/401 |
| 2006/0198798 A1* | 9/2006 | Tichy .................... A01N 59/16 424/53 |
| 2006/0270998 A1* | 11/2006 | Marti .................... A61M 5/425 604/198 |
| 2008/0085290 A1* | 4/2008 | Flugge-Berendes ..... A61K 8/37 424/401 |
| 2008/0086159 A1* | 4/2008 | Zweifler ............... A61M 5/427 606/185 |
| 2009/0326478 A1* | 12/2009 | Salzman ....................... 604/207 |
| 2010/0022965 A1 | 1/2010 | Salzman |
| 2010/0049126 A1 | 2/2010 | Bronfeld et al. |
| 2010/0174237 A1* | 7/2010 | Halaka .......................... 604/114 |
| 2010/0198013 A1* | 8/2010 | Binmoeller ........ A61B 1/00091 600/121 |
| 2010/0211010 A1 | 8/2010 | Wycoki |
| 2010/0211042 A1 | 8/2010 | Casey |
| 2011/0245758 A1 | 10/2011 | Wycoki |
| 2011/0245769 A1 | 10/2011 | Wycoki |
| 2011/0288537 A1 | 11/2011 | Halaka |
| 2012/0016292 A1 | 1/2012 | Goldberg et al. |
| 2012/0065487 A1 | 3/2012 | O'Malley et al. |
| 2012/0130340 A1* | 5/2012 | Knutson ....................... 604/506 |

FOREIGN PATENT DOCUMENTS

| | | |
|---|---|---|
| WO | 98/18512 | 5/1998 |
| WO | 2004/043526 A1 | 5/2004 |
| WO | 2008/081444 A2 | 7/2008 |
| WO | 2008/134580 A2 | 11/2008 |
| WO | 2010/110823 A1 | 9/2010 |

* cited by examiner

DEVICE FOR REDUCING THE PAIN ASSOCIATED WITH INSERTION OF SYRINGE NEEDLE INTO THE SKIN

This application claims priority from European Patent Application No. 12183927.8 filed Sep. 11, 2012, the entire disclosure of which is incorporated herein by reference.

FIELD OF THE INVENTION

The present invention relates to a device for reducing the pain associated with the insertion of the needle of a syringe into the skin.

BACKGROUND AND PRIOR ART

Several devices capable of easing the pain caused by the penetration of a needle of a syringe into the skin of a person for injecting a medicinal substance are already known from the prior art. The international patent application WO 98/18512 A1 can be cited in this regard, which describes such a device that can ease the pain felt by a person during the penetration of a needle of an injection syringe. To do this, this device primarily has a ring at one end intended to come to rest against the skin of a patient in a zone where the injection is to be administered. This ring is supported by tubes, which are connected to an elastic band to define a U-shaped structure. This elastic band is frictionally mounted onto an outer wall of the chamber housing the syringe. A pliable plastic cover is also mounted on the U-shaped structure to conceal the needle from the view of the patient. The ring of the device is thus applied to the skin of the patient before injection of the medicinal substance. The syringe can then slide into the elastic band when pressure is applied by the user of the device in order to cause the needle to penetrate the skin of the person by passing inside the ring.

This type of device described in international patent application WO 98/18512 A1 comprises several elements, which are not simple to assemble together to hide the needle of the syringe from view, on the one hand, and to assure a good sliding movement of the syringe until the needle penetrates into the skin of the patient, on the other hand. This constitutes a disadvantage. Moreover, this device is little suited for proper application to a well-targeted zone of the skin of a patient, in particular it is poorly suited for use in the buccal cavity, which represents another disadvantage.

The patent CH 693 259 also describes a device for reducing the pain generated by the needle of an injection syringe during its insertion through the skin of a patient. To do this, the device comprises a sleeve, in which a part of the body of the syringe with the needle can be housed. An end of the sleeve has an opening, through which the needle of the syringe can pass, and a concave portion delimited by an annular edge to be applied to a determined zone of the skin of a patient for injection of a medicinal substance. This type of device can also be used in the buccal cavity of a patient. However, the simple fact of applying the edge of the end of the sleeve against the skin of a patient with some force does not allow the pain generated by the insertion of the syringe needle into the skin of the patient to be sufficiently eased. This can represent a disadvantage.

SUMMARY OF THE INVENTION

Therefore, the aim of the invention is to remedy the disadvantages of the aforementioned prior art by proposing an improvement to a device for reducing the pain associated with the insertion of the needle of a syringe into the skin.

For this purpose, the invention relates to a device for reducing the pain associated with the insertion of a needle of a syringe into the skin, wherein the device comprises a sleeve, which has a first rear portion to at least partially receive the syringe with the needle and a second front portion fitted with an end part, through which an opening passes for passage of the needle, wherein a front face of the end part is intended to be applied with pressure against the skin of a person before insertion of the needle into the skin, wherein the front face of the end part is arranged to receive an active substance for desensitizing the skin.

Particular embodiments of the device are defined in dependent claims 2 to 9.

An advantage of such a device of the present invention lies in the fact that it allows the skin of a patient to be desensitized locally by mechanical and chemical means before insertion of a needle of a syringe into the skin. This improves the effect achieved by these means for reducing the pain caused by a needle passing through the skin compared to the devices of the prior art. On the one hand, the front face of the end part of the sleeve can be pressed against the skin of a person to reduce the pain at the site of penetration of the needle into the skin. On the other hand, the active substance in the cavity of the end part is applied directly onto the skin of the patient to chemically desensitize the skin at the penetration site.

Because of its structure and its low space requirement, the syringe device allows an operator to administer an injection at any location on the body of a patient, while having a hand free to perform associated tasks. Thus, it is possible with the syringe device to administer an injection into the gums of the patient while guaranteeing a greatly reduced sensation of pain to the patient because of the dual desensitization effect according to the invention.

On this basis, the invention also relates to a sleeve for a device able to reduce the pain associated with the insertion of a needle of a syringe into the skin.

BRIEF DESCRIPTION OF THE DRAWINGS

The invention will be better understood with the assistance of the following description of at least one exemplary embodiment of the device with reference to the attached drawings.

DETAILED DESCRIPTION

In the following description those parts of the device that are well known to a person skilled in the art in this technical field are only described in a simplified manner. The following description primarily relates to the sleeve or covering element of the device, which comprises means able to mechanically and chemically reduce the pain associated with the insertion of a needle of a syringe into the skin of a person.

Figure 1:
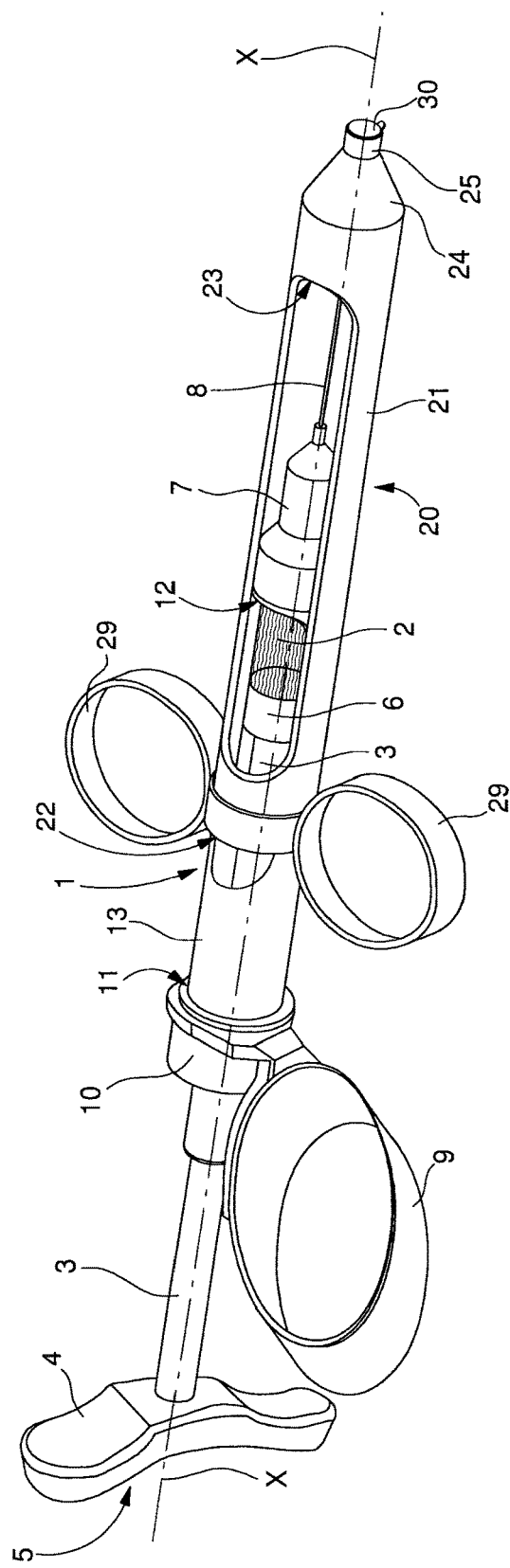
FIG. 1 shows a perspective view representing the device according to the invention wherein the syringe is partially inserted into the covering element that forms a sleeve.

FIG. 1 shows a three-dimensional view of a device for reducing the pain associated with the insertion of a needle 8 of an injection syringe 1 into the skin. This embodiment of the device largely has the features described in the international patent application WO 2004/043526, which is incorporated herein by reference.

This FIG. 1 of the device firstly shows a syringe 1 with a longitudinal axis X that comprises a chamber 2 intended to contain a liquid or medicinal substance to be injected into a patient. A rod 3 that carries an element 4 that has a resting surface 5 at its rear end penetrates the interior of the chamber 2 of the syringe. The rod 3 has a plunger 6 at its front end. This plunger 6 is made from a slightly elastic material and has an outer cross-section that is appreciably larger than the inner cross-section of the chamber 2, so that it ensures a seal between the two parts of the chamber that it delimits. Thus, the plunger 6 is capable of performing translatory movements in the direction of the axis X to transfer the pressure applied by a user on the resting surface 5 to the liquid located in the chamber 2. Thus, this liquid or medicinal substance can be ejected from the syringe 1 during an injection.

The syringe 1 also comprises a socket 7 that is screwed onto a thread or frictionally held at the front end of the chamber 2. The socket 7 carries a needle 8 and in a conventional manner allows needles of different dimensions to be adapted to the chamber 2. A gripping element 9 of the syringe 1 has also been provided at the level of the rear end of the chamber 2. This gripping element 9 can be in the form of a ring or a band as shown that is adapted to receive the thumb of a user of the syringe.

The syringe 1 also comprises a viewing window 12 arranged in an opaque shell 13, in which the chamber 2 is disposed. This viewing window 12 allows a visual control of the level of the liquid to be made during injection.

The syringe 1 of the device is shown in FIG. 1 when partially inserted into an internal space delimited by a sleeve or covering element 20. The sleeve 20 has a first main rear portion 21 generally cylindrical in form, the inner cross-section of which is appreciably larger than the outer cross-section of the chamber 2 of the syringe 1, which is partially formed by the shell 13. The sleeve 20 has a circular opening 22 at its rear end, through which the syringe 1 can be partially inserted before an injection, and gripping means 29 in proximity to its rear end. The syringe 1 can slide into the first portion 21 in a direction along the longitudinal axis X in particular via its shell 13 in contact with the inner cross-section of the first portion 21. The first main portion 21 additionally comprises two elongated windows 23 arranged so as to be diametrically opposed. These windows 23 are provided to cooperate with the viewing window 12 of the syringe when the latter is in place in the internal space of the sleeve 20.

The sleeve 20 also comprises a second portion 24 towards its front end linked to the first main portion 21. This second portion is truncated cone-shaped and terminates in an end part 25. The front face of the end part 25 can have a small surface area, as will be described in more detail below with reference to FIGS. 2a to 2c. This end part has an opening (not shown in FIG. 1) passing through it in the direction of the axis X that commences at the front face and terminates in the internal space of the first main portion 21. This opening is dimensioned to allow passage of the needle 8 of the syringe 1 for an injection.

According to the present invention and as described hereafter, the front face of the end part also comprises an active substance such as an anesthetic. This active or medicinal substance allows desensitization of the location of the skin of a patient to be penetrated by the needle of the syringe in addition to reducing the pain by mechanical pressure of the front face onto the skin of the patient. Before using the device with said sleeve 20, it can be provided to cover the front end of the end part 25 with a cover or preferably a protective cap 30 in order to protect said substance from ambient conditions.

It should also be noted that over its shell 13 the chamber 2 has a short portion 10 with a larger cross-section than its main cross-section to form a shoulder 11. This portion 10 is arranged close to the rear end of the chamber 2. The function of this shoulder 11 is to act as abutment against the rear end of the sleeve 20 to restrict the path of the syringe 1 inside the sleeve 20. Consequently, the shoulder 11 allows reduction of the length of the needle 8 caused to penetrate the skin of the patient.

Figure 2A:
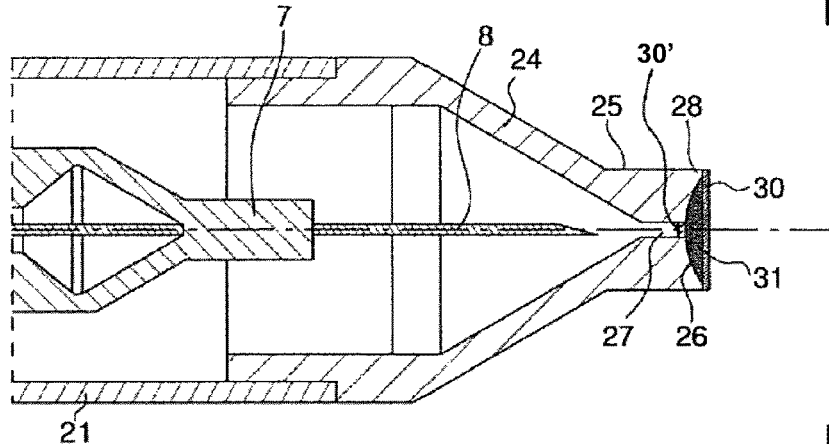
FIGS. 2a to 2c show three views in partial section of the device according to the invention shown in FIG. 1 of the sleeve in an initial position before use, at the time of use and at the instant when the needle passes through the skin of the patient, and FIGS. 3a to 3c each show examples of schematic views of the front face of the sleeve with rectilinear, curved or circular grooves made around the second opening of the front face of the contact zone.
Figure 2B:
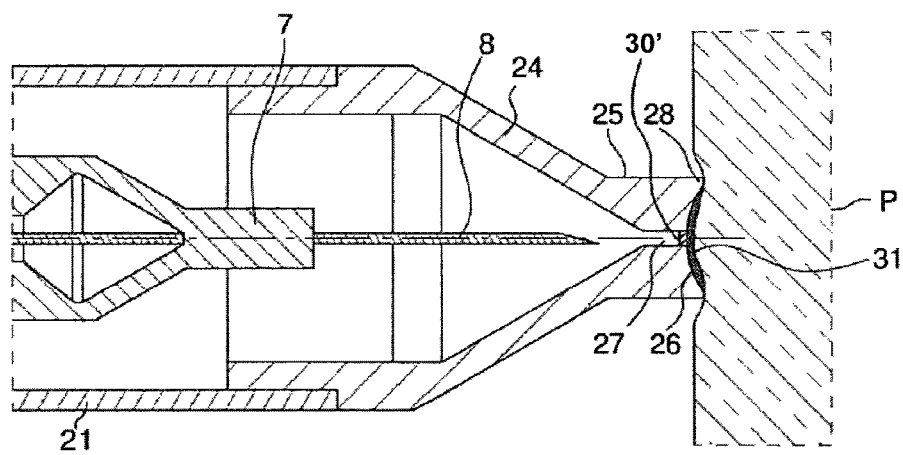
Figure 2C:
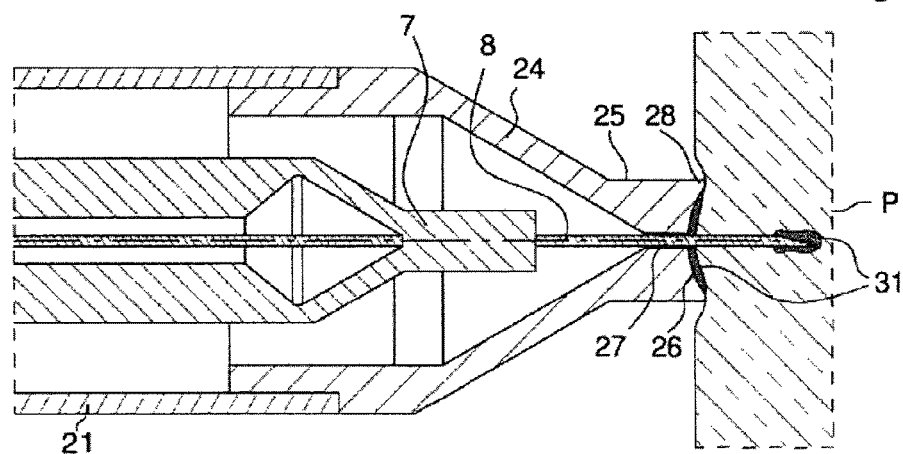

FIGS. 2a to 2c show three views in partial longitudinal section of the sleeve 20 of the device. In the first view in FIG. 2a, the device with the sleeve 20 is shown in an initial position before use. In the second view in FIG. 2b, the device with the sleeve 20 is shown during its use with a part of the front face 26 of the end part 25 of the sleeve 20 in contact with the skin P of a patient. In the third view in FIG. 2c, the device with the sleeve 20 is shown at the instant where the needle 8 of the syringe passes through the skin P of the patient.

Therefore, the sleeve 20 comprises a first portion 21, in front of which a truncated cone-shaped second portion 24 is mounted. This second portion 24 can be fixed to the front part of the first portion 21 by gluing or welding or can be screwed thereto or can also be formed in one piece directly with this first portion 21. This second portion 24 terminates at a tubular end part 25. The first portion 21 and the second portion 24 with the end part 25 can be made from a metallic material or also a plastic material.

The end part 25 of the second portion 24 comprises a front face 26, into which an opening 27 opens. This tubular opening 27 passes through the entire end part 25 from the front face to the internal space of the first main portion 21. This opening 27 is dimensioned so as to have a slightly larger diameter than the diameter of the needle in cross-section in order to freely allow passage of said needle 8 of the syringe.

The front face 26 of this end part 25 is intended to be placed in contact with the skin P of the patient shortly before an injection. This front face 26 comprises a protruding part arranged continuously around the opening 27 in the form of a peripheral edge 28. According to a configuration shown in FIGS. 2a to 2c, this front face 26 can have a concave or ovoid shape between the opening 27 and the edge 28. Said peripheral edge 28 can be continuous or discontinuous and have a semi-circular, square or rectangular cross-section.

As an example, the peripheral edge 28 can be dimensioned to have a width I of between 0.1 and 0.3 mm, preferably equal to 0.25 mm. The diameter of the end part 25 can amount to between 4 and 8 mm, preferably be equal to 5 mm. However, other dimensions can be defined for these elements, permitting a use of the syringe device to administer an injection at the entry to the buccal cavity. The syringe device must therefore be well adapted to such injections in the buccal region, which is particularly difficult to access.

The concave or ovoid shape of the front face 26 defines a cavity from the peripheral edge 28 to the opening 27. According to the present invention it is envisaged to arrange an active substance 31 such as an anesthetic or cooling agent in this cavity. This active substance 31 is intended to be applied to the skin P of a patient at the location where the needle 8 of the syringe penetrates. This active substance is applied to a zone of the skin where the peripheral edge 28 is also pressed mechanically against the skin of the patient, as shown in FIG. 2b. Thus, a dual effect of desensitization of the skin is achieved, on the one hand, by the pressure of the annular peripheral edge 28 on the skin and, on the other hand, by application of the substance to the skin at the location where the needle 8 of the syringe is to penetrate the skin P of the patient. Thus, as a result of this, the sensation of pain associated with the insertion of said needle 8 into the skin can be advantageously reduced by a chemical effect due to said substance and by a mechanical effect as a result of the pressure of the edge 28 against the skin.

The active substance can be in gel form. It can be a "Tropical Anesthetic Gel" type compound, e.g. the compound "Hurricane Tropical Anesthetic Gel" that contains 20% benzocaine, for example, from Beutlich LP Pharmaceuticals. However, other types of active substance are also conceivable as anesthetic to ease the pain associated with the insertion of the needle of a syringe into the skin of a person. A chemical compound that cools the skin of the patient on contact can also be used. This active substance 31 also has the advantage of being partially entrained by the needle 8 of the syringe during its insertion into the skin P, as shown in FIG. 2 c. This also generates a local anesthetic effect directly under the skin of the patient.

Of course, the cavity of the front face 26 can also have a different shape than that shown in FIGS. 2a to 2c with a flat or slightly bent bottom and one or more side walls terminating at the peripheral edge 28. In these conditions more of the medicinal active substance 31 can be housed in said cavity. The front face 26 can also have a multiplicity of raised sections that are either concentric or extend in the radial direction from the opening 27 to the peripheral edge 28. This would allow good adhesion of the active substance 31 arranged in the cavity onto the front face 26

Before its use, the end part 25 of the sleeve with the active substance 31 arranged in the cavity of the front face 26 can be covered by a traditional cover or be closed off by a protective cap 30, as shown in FIG. 2a. This protective cap must be removed at the instant of use of the device. This 15 enables protection of said active substance 31 from the ambient conditions in which said syringe device is kept. Conversely, it is not necessarily envisaged to arrange a brittle membrane 30' on the opening 27 so as not to dull the point of the needle 8 of the syringe during passage.

Figure 3A:
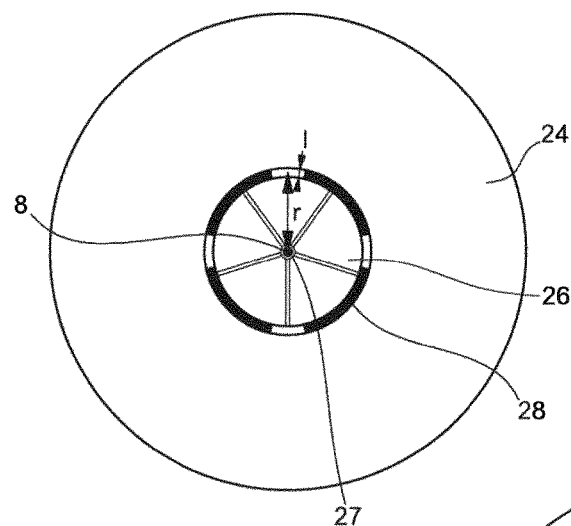
Figure 3B:
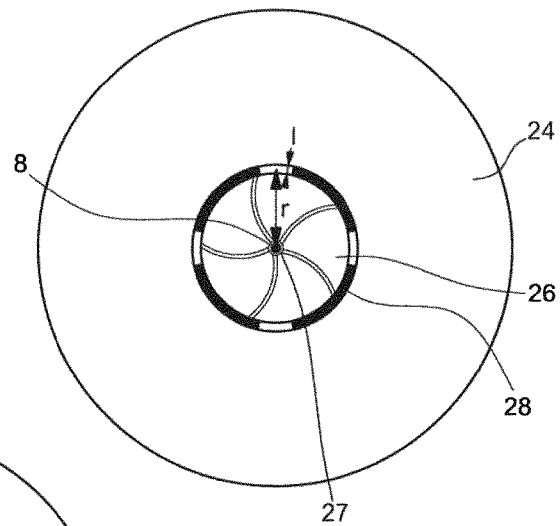
Figure 3C:
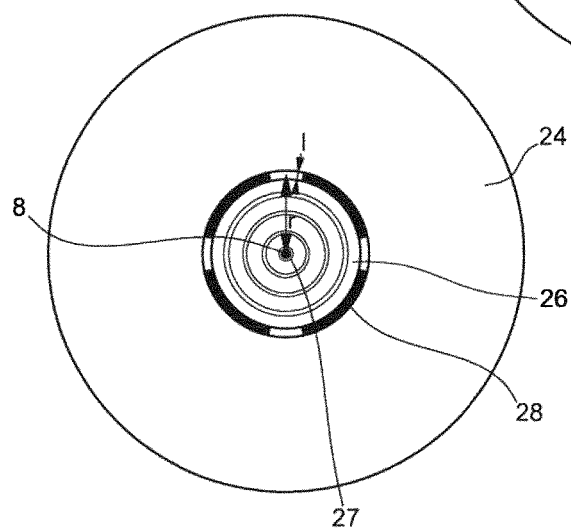

On the basis of the description just outlined, several variants of the device for reducing the pain associated with the insertion of a needle of a syringe into the skin can be designed by a person skilled in the art without departing from the scope of the invention as defined in the claims. The syringe device can be used to take blood samples instead of administering injections, benefiting from the mechanical and chemical dual effect of desensitizing or anaesthetize the skin. The syringe device can be provided to facilitate an injection into the buccal cavity of a patient. As shown in FIGS. 3a-3c, it can be provided that rectilinear, curved or circular grooves are made around the second opening of the front face to receive the active substance. This active substance can equally be in liquid or powder form.

What is claimed is:

1. A device comprising: a syringe with a needle, a sleeve on the syringe, and an active or medicinal substance on the sleeve for reducing the pain by a desensitization mechanical pressure and chemical dual effect associated with the insertion of the needle of the syringe into skin of a person, wherein the sleeve, which has a first rear portion to at least partially receive a syringe with a needle and a second front portion fitted with an end part, includes an opening through which the needle passes, wherein a front face of the end part includes at least one cavity between the opening and a peripheral edge of the end part, in which the active or medicinal substance in the form of a gel to desensitize the location of the skin of the person to be penetrated by the needle, is located and adhered, wherein the peripheral edge of the front face of the end part is configured to be applied with pressure against the skin of a person before insertion of the needle into the skin, wherein the front face of the end part comprises rectilinear, curved or circular grooves, in which the active or medicinal substance is disposed and adhered wherein said active or medicinal substance in the cavity is configured to be in direct contact with the skin of the person before an injection in order to have the mechanical pressure and chemical dual effect of desensitization at the site of penetration of the needle into the skin, wherein a protective cap is fixed onto the peripheral edge to enclose and to protect, before use of the device, the active or medicinal substance in the cavity of the front face of the end part, said protective cap to be removed at an instant of use of the device, wherein in an initial position before use of the device, the needle of the syringe is situated in an internal space of the first rear portion of the sleeve not in direct contact with the active or medicinal substance, and wherein at the instant of use of the device, the needle extends through the opening and contacts the active or medicinal substance which is partially entrained under the skin of the person by the needle of the syringe during insertion into the skin and generates a local anesthetic effect directly under the skin of the patient.

2. The device according to claim 1, wherein the active or medicinal substance is an anesthetic substance.

3. The device according to claim 1, wherein the active or medicinal substance is a cooling substance.

4. The device according to claim 1, wherein the active or medicinal substance is disposed in the whole cavity from the opening to the peripheral edge.

5. The device according to claim 1, wherein the cavity is concave or ovoid in shape between the opening and peripheral edge, which is a ring-shaped peripheral edge.

6. A device comprising: a syringe with a needle, a sleeve on the syringe, and an active or medicinal substance on the sleeve for reducing the pain by a desensitization mechanical pressure and chemical dual effect associated with the insertion of the needle of the syringe into skin of a person, wherein the sleeve, which has a first rear portion to at least partially receive the syringe with a needle and a second front portion fitted with an end part, includes an opening through which the needle passes, wherein a front face of the end part includes at least one cavity between the opening and a peripheral edge of the end part, in which the active or medicinal substance in the form of a gel to desensitize the location of the skin of the person to be penetrated by the needle, is located and adhered, wherein the front face of the end part comprises rectilinear, curved or circular grooves, in which the active or medicinal substance is located and adhered, wherein the peripheral edge of the front face of the end part is configured to be applied with pressure against the skin of a person before insertion of the needle into the skin, wherein said active or medicinal substance in the cavity is configured to be in direct contact with the skin of the person before an injection in order to have the mechanical pressure and chemical dual effect of desensitization at the site of penetration of the needle into the skin, wherein a brittle membrane is arranged on the opening so as not to dull the point of the needle of the syringe during passage, said opening passing through the entire end part from the front face to an internal space of the second front portion, wherein the brittle membrane encloses and protects, before use of the device, the active or medicinal substance in the cavity of the front face of the end part, wherein in an initial position before use of the device, the needle of the syringe is situated in an internal space of the first rear portion of the sleeve not in direct contact with the active or medicinal substance, and wherein at an instant of use of the device, the needle extends through the opening and contacts the active or medicinal substance which is partially entrained under the skin of the person by the needle of the syringe during insertion into the skin and generates a local anesthetic effect directly under the skin of the patient.

7. A device comprising:
   a syringe with a needle, a sleeve on the syringe, and an active or medicinal substance on the sleeve for reducing the pain by a desensitization mechanical pressure and chemical dual effect associated with the insertion of the needle of the syringe into skin of a person,
   wherein the sleeve, which has a first rear portion to at least partially receive a syringe with a needle and a second front portion fitted with an end part, includes an opening through which the needle passes,
   wherein a front face of the end part includes at least one cavity between the opening and a peripheral edge of the end part, in which the active or medicinal substance in the form of a gel to desensitize a location of the skin of the person to be penetrated by the needle, is located and adhered,
   wherein the peripheral edge of the end front face of the end part is configured to be applied with pressure against the skin of a person before insertion of the needle into the skin,
   wherein said active or medicinal substance in the cavity is configured to be in direct contact with the skin of the person before an injection in order to have the mechanical pressure and chemical dual effect of desensitization at the site of penetration of the needle into the skin,
   wherein in an initial position before use of the device, the needle of the syringe is situated in an internal space of the first rear portion of the sleeve not in direct contact with the active or medicinal substance,
   wherein at an instant of use of the device, the needle extends through the opening of the second front portion and contacts the active or medicinal substance which is partially entrained under the skin of the person by the needle of the syringe during insertion into the skin and generates a local anesthetic effect directly under the skin of the patient, and
   wherein the front face of the end part comprises rectilinear, curved or circular grooves, in which the active or medicinal substance is disposed and adhered.

8. The device according to claim 7, wherein the opening in the second front portion is dimensioned so as to have a slightly larger diameter than a diameter of the needle.

9. The device according to claim 7, wherein the cavity of the front face has one or more side walls terminating at the peripheral edge in order to have more of the active or medicinal substance housed in the cavity.

10. The device according to claim 7, wherein the substance is an anesthetic gel.

11. The device according to claim 7, wherein the substance is an anesthetic gel having 20% benzocaine.

12. The device according to claim 7, wherein the cavity of the front face has a flat or slightly bent bottom and one or more walls terminating at the peripheral edge.

13. The device according to claim 12, wherein the front face has a multiplicity of raised sections which are concentric or extend in radial direction from the opening to the peripheral edge.

14. A sleeve for a device able to reduce pain by desensitization dual effect associated with an insertion of a needle of a syringe into skin of a person, the sleeve comprising:
   a first rear portion to at least partially receive the syringe with the needle; and
   a second front portion fitted with an end part, through which an opening passes for passage of the needle,
   wherein a front face of the end part includes at least one cavity between the opening and a peripheral edge of the end part, in which an active or medicinal substance in the form of a gel to desensitize the location of the skin of the person to be penetrated by the needle, is located and adhered,
   wherein the peripheral edge of the front face of the end part is configured to be applied with pressure against the skin of a person before insertion of the needle into the skin, and the active or medicinal substance in the cavity is configured to be in direct contact with the skin of the person before an injection in order to have a mechanical pressure and chemical dual effect of desensitization at the site of penetration of the needle into the skin, and able to be partially entrained under the skin of the person by a needle during insertion into the skin, and
   wherein the front face of the end part comprises rectilinear, curved or circular grooves, in which the active or medicinal substance is disposed and adhered.

* * * * *